United States Patent [19]

Rölla et al.

[11] Patent Number: 5,422,098
[45] Date of Patent: Jun. 6, 1995

[54] DENTIFRICE INHIBITING DENTAL PLAQUE

[76] Inventors: Gunnar Rölla, Kragsvei 13, 0391 Oslo; Jan E. Ellingsen, Skogbrynet 17b, 0283 Oslo, both of Norway

[21] Appl. No.: 930,551
[22] PCT Filed: Mar. 4, 1991
[86] PCT No.: PCT/NO91/00032
  § 371 Date: Sep. 28, 1992
  § 102(e) Date: Sep. 28, 1992
[87] PCT Pub. No.: WO91/13608
  PCT Pub. Date: Sep. 19, 1991

[30] Foreign Application Priority Data

May 5, 1990 [NO] Norway .................. 901031

[51] Int. Cl.$^6$ .................. A61K 7/16
[52] U.S. Cl. .................. 424/49
[58] Field of Search .................. 424/49

[56] References Cited

U.S. PATENT DOCUMENTS

| | | | |
|---|---|---|---|
| 2,806,814 | 9/1957 | Richter | 424/49 |
| 3,507,955 | 4/1970 | Osipow | 424/54 |
| 4,022,880 | 5/1977 | Vinson et al. | 424/49 |
| 4,202,879 | 5/1980 | Shelton | 424/66 |
| 4,414,200 | 11/1983 | Murphy et al. | 424/63 |
| 5,078,988 | 1/1992 | Lin et al. | 424/49 |
| 5,188,822 | 2/1993 | Viccaro et al. | 424/52 |
| 5,254,332 | 10/1993 | Grezcyn et al. | 424/66 |

FOREIGN PATENT DOCUMENTS

| | | |
|---|---|---|
| 0161899 | 11/1985 | European Pat. Off. . |
| 0220890 | 5/1987 | European Pat. Off. . |
| 0371551 | 6/1990 | European Pat. Off. . |
| 0373688 | 6/1990 | European Pat. Off. . |
| 0376363 | 7/1990 | European Pat. Off. . |
| 686429 | 1/1953 | United Kingdom . |
| 789851 | 1/1958 | United Kingdom . |

OTHER PUBLICATIONS

Chemical Abstracts 81:20897y (1974).

*Primary Examiner*—Ronald W. Griffin
*Attorney, Agent, or Firm*—Wenderoth, Lind & Ponack

[57] ABSTRACT

Dentifrice comprising a liquid silicone oil and a fat-soluble antibacterial agent dissolved therein either directly or indirectly after dissolution of the antibacterial agent in an organic solvent. The dentifrice is useful for protection of teeth against plaque formation due to a slow release of the antibacterial agent into the saliva.

5 Claims, 2 Drawing Sheets

DENTIFRICE INHIBITING DENTAL PLAQUE

The present invention relates to dentifrices having an improved effect against the growth of plaque on teeth. The dentifrices may be in the form of powders, tooth pastes, chewing gum etc., but tooth pastes are normally preferred. An important constituent of the dentifrices of the invention is organopolysiloxanes.

From Britist Patent No. 686,429 it is known to incorporate organopolysiloxanes in dentifrices to prevent the adhesion of or facilitate the removal of tars, stains, tartar and the like from teeth.

British Patent No. 789,851 discloses oral hygiene compositions containing an organopolysiloxane and a higher aliphatic acyl amide of an amino carboxylic acid compound which is preferably a water-soluble carboxylate salt. British Patent No. 1,194,885 describes the addition of a quaternized tertiary cyclic amine in which a $C_{8-22}$ aliphatic radical is attached to the quaternary nitrogen atom, to a dimethyl polysiloxane to improve the adherence of the silicone film to the teeth.

A similar solution is suggested in U.S. Pat. No. 4,161,518 where quaternary ammonium groups are incorporated in an organosiloxane molecule.

EP patent application, publication No. 0376363 discloses the use of aminoalkyl silicones and sarcosinate surfactants to prevent staining of teeth and in preventing caries, particularly in conjunction with antimicrobials which have a tendency to stain teeth.

Bacterial growth on teeth is a well known problem. The two major dental diseases, caries and periodontitis, are initiated and develop only in the presence of dental plaque. Dental plaque consists of dense aggregates of bacteria which attach to the tooth enamel, mainly in the interproximal area, or along the gingival margin. The enamel disintegrates when sucrose or other fermentable carbohydrates are consured; the plaque bacteria produce organic acids (mainly lactate) in this situation which cause dissolution of the hydroxyapatite of which enamel mainly consists. Dental plaque may also produce enzymes, toxins or antigens which may cause inflammation of the gingival tissue. A chronic inflammation under certain conditions lead to loss of the alveolar bone which supports the teeth, and subsequent tooth-loss.

Inhibition of adsorption of bacteria to dental enamel will thus have the potential to prevent both dental caries and periodonal disease. The mecanism by which the bacteria bind to enamel is not well understood. The inhibition of plaque formation obtained up to now has been caused by antibacterial agents with a longterm effect in the mouth. These substances interfere with bacterial growth rather than with the absorption of bacteria to enamel. Such substances have untoward side effects like staining of teeth and tongue, and unpleasant taste, and they cause a general decrease of the number of bacteria on the oral cavity. Substances which solely reduce the growth of plaque on the teeth by interference with their binding mechanisms have not yet been found.

As it will appear from the above it is previously known that silicone oil binds to the enamel surface of the teeth, and provides a hydrophobic surface thereon by forming a thin layer of oil which covers the surface for several hours after a single application. We have now surprisingly found that this layer of silicone oil can serve as a reservoir of certain antibacterial agents which are soluble in silicon oil directly, or indirectly, after an initial step where the antibacterial agent is dissolved in another organic solvent, and the resulting solution is then dissolved in silicon oil.

Thus, the invention provides a dentifrice which comprises silicone oil and a fat-soluble antibacterial agent dissolved therein, either directly or after dissolution of the anti-bacterial agent in an organic solvent.

Suitable silicone oils are e.g. the fluid organopolysiloxanes described in the above mentioned British Patent No. 789,851. A preferred class comprises the diphenyl or di($C_{1-4}$)alkyl polysiloxanes, in particular liquid dimethylpolysiloxane.

Suitable antibacterial agents are antiseptic phenols, in particular triclosan (also called inpasan) (5-chloro-2-(2,4-dichlorophenoxy)phenol, which may be used in amounts varying from 0.01%, based on the silicone oil, to the maximum amount soluble in the silicone oil.

If the antibacterial agent is insoluble in the silicone oil, it may first be dissolved in a suitable organic solvent such as ethanol, and the resulting solution is then dissolved in the silicone oil.

It is important that the antibacterial agent is non-toxic and is soluble in the silicone oil used and of very limited solubility in water. Trichosan is such an agent and is also known to decrease plaque formation (but not dissolved in polysiloxanes), see e.g. C.A. vol 81 (1974) no. 20897y. Similarly it is important that the polysiloxane is non-toxic, such as Dow Corning 200 which has been used in the examples.

When the dentifrice is applied to the teeth, the silicone oil forms a hydrophobic layer which serves as a reservoir for the antibacterial agent. As known in the art, the silicone oil in itself will provide some protection due to its hydrophobic character. However we have now found that the protection will be much better when the antibacterial agent is dissolved therein and subsequently slowly released into the environment. The treatment furthermore inhibits calculus formation, probably due to the smooth silicone oil-covered surface which prevents the fixation of calculus to the teeth, and triclosan which inhibit plaque formation. Calculus constitutes in fact calcified plaque.

EXPERIMENTAL

Six students painted their teeth 2× daily with Q-tips moisted with either water, silicone oil (dimethylpolysiloxane) alone, 0.3% triclosan in water or silicon oil +0.3% triclosan. Their teeth were pumiced at the start of the study and plaque was scored on each surface of all the teeth after 4 days. No other form of oral hygiene was allowed. The test persons chewed six pieces of chewing gum containing 75% sucrose per day to increase plaque formation. The results are shown in FIGS. 1-4. Score 0 is given to surfaces with no plaque. Score 1 is given to surfaces where visible plaque is seen on the probe after running the poin of the probe along the gingival margin of each tooth. Score 2 indicates visible plaque, and score 3 plaque up to 2 mm above the gingival margin.

Figure 1:
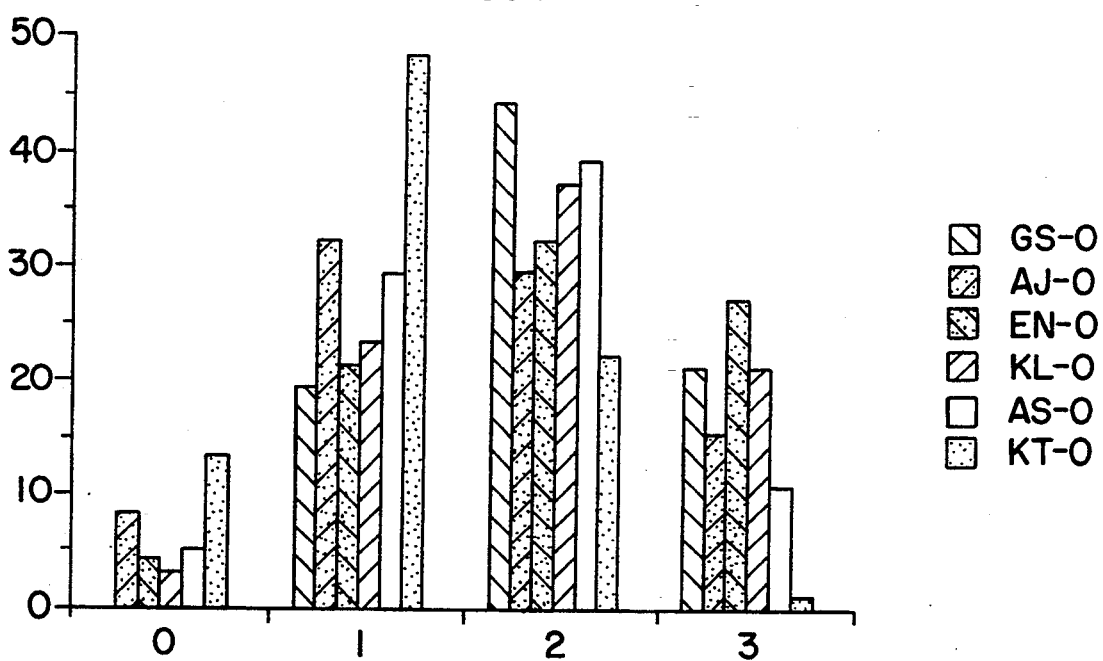
FIG. 1 illustrates the score for each of the six test persons after painting their teeth with water only.
Figure 2:
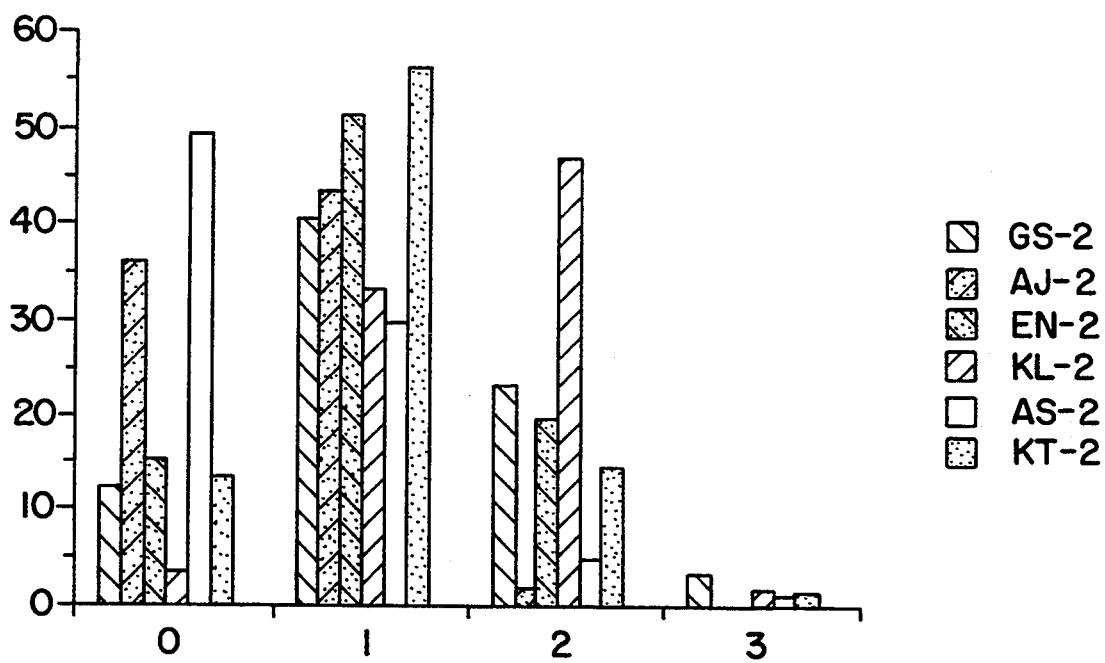
FIG. 2 illustrates the score for the same persons after treatment with dimethylpolysiloxane.
Figure 3:
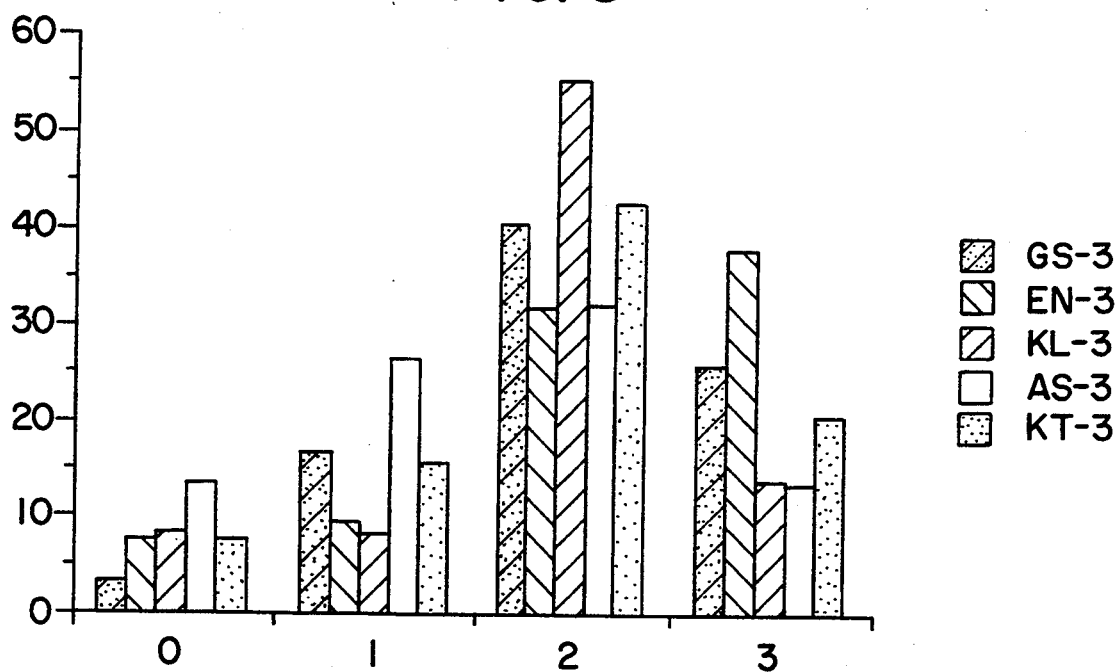
FIG. 3 illustrates the score of the same person (−1) after treatment with 0.3% of trichlosan suspended in water.
Figure 4:
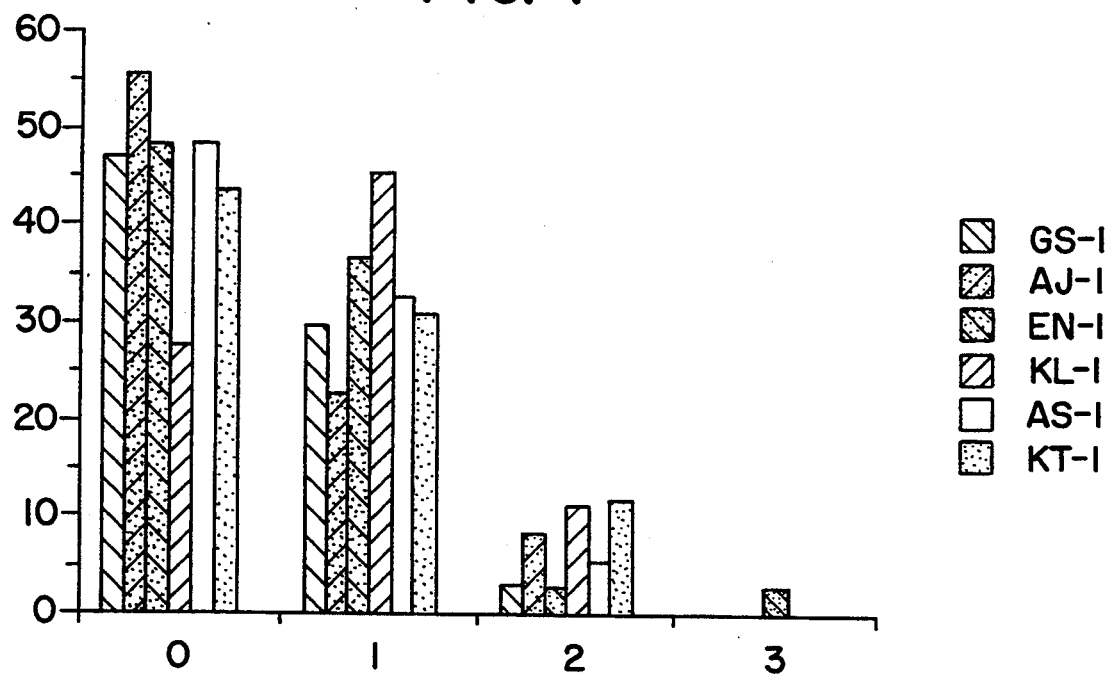
FIG. 4 illustrates the score after treatment with dimethylpolysiloxane containing 0.3% triclosan.

The pairs of letters of the right hand side of the graph represent the initials of the test persons, and the subsequent number is the experiment involved. The abscissa indicates the score distribution, and the ordinate represents the number of surfaces having the indicated score for each test person. While triclosan alone gives no improvement, it will be seen that the silicone oil results in an increased number of scores of 0 and 1 compared with the control. Silicone oil +0.3% triclosan gives a marked improvement in plaque scores compared with the control (FIG. 1) and the silicone oil treated teeth (FIG. 2).

The teeth of the group treated with silicone oil+triclosan were shiny clean. Small amounts of plaque occasionally present was easily removed with a compressed air syringe.

Five individuals who were selected on the basis that they produced high amounts of calculus in their mouths were selected for the study. They used a toothpaste which contained 0.3% triclosan and silicone oil, and calculus was again scored after one month. The amounts of calcululs formed were markedly reduced and the small amount present was easily removed since the calcululs was only loosely attached to the teeth.

In an in vitro experiment glass test tubes were treated with either water, silicone oil or silicone oil +0.3% triclosan 0.5 ml of a 1 day old culture of strep. Mutans and 5 ml of glucose broth medium +5% sucrose was then added to the tubes. Abundant growth and bacteria sticking to the glass wall was seen in the water treatment tubes. The tubes treated with silicone oil alone showed reduced growth, only a few bacteria adhering to the glass surface. However, the test tube which had been pretreated with silicone oil containing 0.5% triclosan showed only negligible growth and no bacteria on the glass surface.

These experiments considered together indicate that the teeth and the glass tubes acquire a hydrophobic surface layer with antibacterial activity which inhibit adsorption of bacteria when treated with silicone oil and triclosan. This is a unique effect which is not obtained by any previously known clinical procedure in preventive dentistry. It is caused by the fact that the polysiloxane acts as a roservoir for the antibacterial agent (triclosan) dissolved therein. Small amounts of the anti-bacterial agent are slowly released from the polysiloxane film adhering to the teeth and will therefore effectively inhibit the formation of plaque due to the limited solubility in water.

We claim:

1. A dentifrice comprising a liquid diphenyl-polysiloxane or a dialkyl-polysiloxane and a fat-soluble antiseptic phenol of very limited water-solubility dissolved therein.

2. The dentifrice according to claim 1, wherein the dialkyl-polysiloxane is a di($C_{1-14}$)alkyl-polysiloxane.

3. The dentifrice according to claim 2, wherein the di($C_{1-4}$)alkyl-polysiloxane is a dimethyl-polysiloxane.

4. The dentifrice according to any of claims 1 to 3, wherein the antiseptic phenol is triclosan (5-chloro-2-(2,4-dichlorophenoxy)phenol).

5. The dentrifice according to claim 1 wherein an organic solvent for the phenol is also present.

* * * * *